(12) United States Patent
Vriamont et al.

(10) Patent No.: US 11,584,118 B2
(45) Date of Patent: Feb. 21, 2023

(54) LITHOGRAPHIC PRINTING PLATE PRECURSOR

(71) Applicant: AGFA OFFSET BV, Mortsel (BE)

(72) Inventors: Nicolas Vriamont, Mortsel (BE); Thomas Billiet, Mortsel (BE); Johan Loccufier, Mortsel (BE); Elke Dom, Mortsel (BE)

(73) Assignee: AGFA Offset BV, Mortsel (BE)

( * ) Notice: Subject to any disclaimer, the term of this patent is extended or adjusted under 35 U.S.C. 154(b) by 0 days.

(21) Appl. No.: 17/292,568

(22) PCT Filed: Oct. 21, 2019

(86) PCT No.: PCT/EP2019/078493
§ 371 (c)(1),
(2) Date: May 10, 2021

(87) PCT Pub. No.: WO2020/094368
PCT Pub. Date: May 14, 2020

(65) Prior Publication Data
US 2022/0009219 A1    Jan. 13, 2022

(30) Foreign Application Priority Data
Nov. 9, 2018 (EP) .................................. 18205373

(51) Int. Cl.
*B41C 1/10* (2006.01)
*C07C 233/56* (2006.01)
*G03F 7/09* (2006.01)

(52) U.S. Cl.
CPC .......... *B41C 1/1016* (2013.01); *C07C 233/56* (2013.01); *G03F 7/092* (2013.01)

(58) Field of Classification Search
CPC .................................................. B41C 1/1016
See application file for complete search history.

(56) References Cited

U.S. PATENT DOCUMENTS

| 9,482,954 | B2 * | 11/2016 | Loccufier ................ G03F 7/027 |
| 2014/0057204 | A1 * | 2/2014 | Werner ................ B41C 1/1008 430/273.1 |
| 2016/0282718 | A1 * | 9/2016 | Steenackers ............ G03F 7/031 |

FOREIGN PATENT DOCUMENTS

| EP | 0309619 A1 | 4/1989 |
| EP | 3170662 A1 | 5/2017 |
| EP | 3239184 A1 | 11/2017 |
| WO | 2014/198820 A1 | 12/2014 |
| WO | 2014/198823 A1 | 12/2014 |

OTHER PUBLICATIONS

International Search Report dated Jan. 7, 2020 relating to PCT/EP2019/078493, 4 pages.
Written Opinion dated Jan. 7, 2020 relating to PCT/EP2019/078493, 5 pages.

* cited by examiner

*Primary Examiner* — Chanceity N Robinson
(74) *Attorney, Agent, or Firm* — Leydig, Voit & Mayer, Ltd.

(57) ABSTRACT

A lithographic printing plate precursor including a photopolymerisable coating and an overcoat layer provided on top of said layer, characterized in that the overcoat layer includes a compound comprising at least one moiety having a structure according to Formula (I): (I).

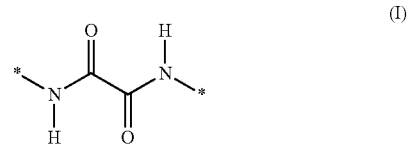

20 Claims, No Drawings

LITHOGRAPHIC PRINTING PLATE PRECURSOR

REFERENCE TO RELATED APPLICATIONS

This application is a 371 National Stage Application of PCT/EP2019/078493, filed Oct. 21, 2019, which claims the benefit of European Application No. 18205373.6, filed Nov. 9, 2018, the contents of which are incorporated by reference herein in their entirety.

TECHNICAL FIELD

The invention relates to a novel overcoat of a photopolymer printing plate.

BACKGROUND ART

Lithographic printing presses use a so-called printing master such as a printing plate which is mounted on a cylinder of the printing press. The master carries a lithographic image on its surface and a print is obtained by applying ink to said image and then transferring the ink from the master onto a receiver material, which is typically paper. In conventional, so-called "wet" lithographic printing, ink as well as an aqueous fountain solution (also called dampening liquid) are supplied to the lithographic image which consists of oleophilic (or hydrophobic, i.e. ink-accepting, water-repelling) areas as well as hydrophilic (or oleophobic, i.e. water-accepting, ink-repelling) areas. In so-called driographic printing, the lithographic image consists of ink-accepting and ink-adhesive (ink-repelling) areas and during driographic printing, only ink is supplied to the master.

The so-called "analogue" printing plates are generally obtained by first applying a so-called computer-to-film (CtF) method, wherein various pre-press steps such as typeface selection, scanning, color separation, screening, trapping, layout and imposition are accomplished digitally and each color selection is transferred to graphic arts film using an imagesetter. After processing, the film can be used as a mask for the exposure of an imaging material called plate precursor and after plate processing, a printing plate is obtained which can be used as a master. Since about 1995, the so-called "computer-to-plate" (CtP) method has gained a lot of interest. This method, also called "direct-to-plate", bypasses the creation of film because the digital document is transferred directly to a printing plate precursor by means of a platesetter. A printing plate precursor for CtP is often called a digital plate.

The support of the lithographic printing plates are typically aluminum supports which have a hydrophilic surface or on which a hydrophilic layer has been provided. This hydrophilic surface and/or layer should improve the water acceptance of the non-printing areas of a lithographic printing plate and the repulsion of the printing ink in these areas. During developing the soluble portions of the coating should be easily removed whereby the surface of the support remains substantially residue-free so that clean background areas are obtained during printing.

Digital plates can roughly be divided in three categories: (i) silver plates, working according to the silver salt diffusion transfer mechanism; (ii) photopolymer plates containing a photopolymerisable composition that hardens upon exposure to light and (iii) thermal plates of which the imaging mechanism is triggered by heat or by light-to-heat conversion.

Photopolymer printing plates rely on a working-mechanism whereby the coating—which typically includes free radically polymerisable compounds—hardens upon exposure, optionally followed by a heating step to enhance or to speed-up this process. "Hardens" means that the coating becomes insoluble or non-dispersible in the developing solution and may be achieved through polymerization and/or crosslinking of the photosensitive coating upon exposure to light. Conventional photopolymer plates were exposed with ultraviolet light from a lamp through a separate photomask film having a predetermined imaging pattern that is placed between the light source and the plate. Nowadays laser sources are generally used to imagewise expose printing plate precursors that are sensitized to a corresponding laser wavelength, allowing the elimination of the photomask film. However, such laser imagable plates often have the drawback of limited room light stability and/or should have a high photospeed (sensitivity) because of the limited power of current laser imagers. Photopolymer plate precursors can be sensitized to blue, green or red light i.e. wavelengths ranging between 450 and 750 nm, to violet light i.e. wavelengths ranging between 350 and 450 nm or to infrared light i.e. wavelengths ranging between 750 and 1500 nm.

Photopolymer plates typically contain a polymerizable monomer, a binder, a photoinitiator and a sensitizing dye. In general, a toplayer or protective overcoat layer over the imageable layer which acts as an oxygen barrier layer is required to maintain the sensitivity of the plate. A toplayer typically includes water-soluble or water-swellable polymers such as for example polyvinylalcohol. Besides acting as barrier for oxygen, the toplayer should best be easily removable during processing and be sufficiently transparent for actinic radiation, e.g. from 300 to 450 nm or from 450 to 750 nm or from 750 to 1500 nm.

The classical work flow of photopolymer plates involves first an exposure step of the photopolymer printing plate precursor in a platesetter, followed by an optional pre-heat step, a wash step of the protective overcoat layer, an alkaline developing step, and a rinse and gum step. Over the past years, there is a clear evolution in the direction of a simplified workflow where the processing and gumming step are carried out in one single step. Alternatively, on-press processing wherein the plate is mounted on the press and the coating layer is developed by interaction with the fountain and ink that are supplied to the cylinder during the press run, has become very popular. During the first runs of the press, the non-image areas are removed from the support and thereby define the non-printing areas of the plate.

However, the developing step becomes much more critical when the alkaline developer is replaced by a gum solution and/or by an on-press processing. Indeed, the hydrophilic polymers in the protective overcoat layer may result in a problematic viscosity increase of the gum solution and/or the fountain solution limiting the exhaustion behavior. This viscosity increase may cause an unacceptable formation of sludge, speckles on the plate and/or deposits in the clean-out unit, and this already at low exhaustion level. Sludge formation such as salted-out compounds, precipitated or flocculated ingredients and/or other undissolved compounds may cause problems such as clogging of pumps, deposit on the exit and/or other rollers and/or, build-up on heater elements and/or the need for intensive cleaning/maintenance of processing vessels. Sludge may also be deposited on the printing plate which impairs the images formed thereon. Moreover, lithographic printing plate precursors which are processed on-press with fountain and ink, or which are processed and gummed in a single step by using a gumming solution, often show an insufficient clean out behaviour and/or roll-up performance. Insufficient roll-up performance means that the ink acceptance at the printing areas is too weak during the start-up of the printing process. This too low take-up of ink results in a too low optical density at the printing areas on the first number of printed sheets. It is desirable that this number of these "unusable" printed sheets is as low as possible in order to reduce the waste of paper in the start-up of the printing process.

SUMMARY OF INVENTION

It is an object of the present invention to provide a negative-working lithographic printing plate precursor including a photopolymerisable layer which is characterized by an excellent gum and/or on-press processability whereby the formation of sludge and/or precipitate and/or deposit materials during processing is minimised.

This object is realized by the printing plate precursor defined in claim 1 with preferred embodiments defined in the dependent claims. The invention has the specific feature that the printing plate precursor includes an overcoat layer including a compound comprising at least one moiety having a structure according to Formula (I):

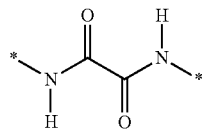

It was surprisingly found that the solubility of the overcoat layer of the present invention in a developer solution and/or during on press processing, is significantly improved, and the viscosity increase during development of the developing solution and/or fountain solution is minimised. With an improved solubility of the overcoat layer is meant that its ingredients dissolve faster and/or have a reduced tendency to form precipitate (i.e. organic sludge) and/or deposit materials.

It is a further object of the present invention to provide a method for making a lithographic printing plate comprising the steps of:

image-wise exposing the printing plate precursor including the coating as defined above to light radiation;

developing the exposed precursor.

Other features, elements, steps, characteristics and advantages of the present invention will become more apparent from the following detailed description of preferred embodiments of the present invention. Specific embodiments of the invention are also defined in the dependent claims.

DESCRIPTION OF EMBODIMENTS

The Overcoat

The lithographic printing precursor of the present invention includes on a support a photopolymerisable coating and a top layer provided thereon. The top layer, also referred to herein as "protective layer", "overcoat" or "overcoat layer", acts as a barrier layer for gasses, more specific as an oxygen-barrier layer, and comprises a compound including at least one moiety having a structure according to Formula (I):

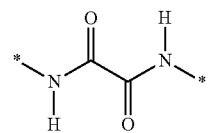 [SMILES: *NC(=O)C(=O)N*]

wherein
* denote the linking positions to the rest of the structure.

The compound including at least one moiety having a structure according to Formula (I) is further also referred to herein as "the inventive compound".

The compound according to the present invention can be a low molecular weight compound, an oligomer, or a polymer. The compound according to the present invention may contain one moiety according to Formula (I), preferably 2 to 10 moieties according to Formula (I), more preferably 4 to 8 moieties according to Formula (I) and most preferably two, three or four moieties according to Formula (I).

The compound according to the present invention, is preferably represented by Formula (II):

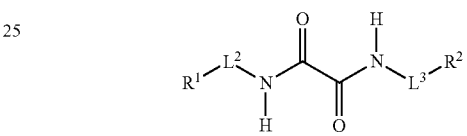

wherein
$R^1$ and $R^2$ independently represent a terminal group; and
$L^2$ and $L^3$ independently represent a divalent linking group.

The terminal groups $R^1$ and $R^2$ are preferably represented by hydrogen, an optionally substituted alkyl or cycloalkyl group, an optionally substituted aryl group, an optionally substituted aralkyl group or an optionally substituted heteroaryl group.

Suitable alkyl groups herein include 1 or more carbon atoms such as for example C1 to C22-alkyl groups, more preferably C1 to C12-alkyl groups and most preferably C1 to C6-alkyl groups. The alkyl group may be linear or branched such as for example methyl, ethyl, propyl (n-propyl, isopropyl), butyl (n-butyl, isobutyl, t-butyl), pentyl, 1,1-dimethyl-propyl, 2,2-dimethylpropyl and 2-methylbutyl, or hexyl.

Suitable cycloalkyl groups herein are non-aromatic, homocyclic groups containing carbon atoms and may be monocyclic- or polycyclic. Examples include cyclopentyl, cyclohexyl or adamantyl.

Suitable aryl groups herein include for example phenyl, naphthyl, benzyl, tolyl, ortho-meta- or para-xylyl, anthracenyl or phenanthrenyl.

Suitable aralkyl groups herein include for example phenyl groups or naphthyl groups including one, two, three or more C1 to C6-alkyl groups.

Suitable heteroaryl groups herein are preferably monocyclic- or polycyclic aromatic rings comprising carbon atoms and one or more heteroatoms in the ring structure. Preferably 1 to 4 heteroatoms independently selected from nitrogen, oxygen, selenium and sulphur and/or combinations thereof. Examples include pyridyl, pyrimidyl, pyrazoyl, triazinyl, imidazolyl, (1,2,3)- and (1,2,4)-triazolyl, tetrazolyl, furyl, thienyl, isoxazolyl, thiazolyl and carbazoyl.

More preferably $R^1$ and $R^2$ are independently represented by hydrogen or an optionally substituted alkyl, aryl or aralkyl group, and/or combination thereof.

Most preferably, $R^1$ and $R^2$ independently represent hydrogen or methyl.

The alkyl, cycloalkyl, aralkyl, aryl or heteroaryl groups may include one or more substituents. The optional substituents on the alkyl, cycloalkyl, aralkyl, aryl or heteroaryl groups are preferably selected from an alkyl group such as a methyl, ethyl, n-propyl, isopropyl, n-butyl, 1-isobutyl, 2-isobutyl and tertiary-butyl group; an ester, amide, ether, thioether, ketone, aldehyde, sulfoxide, sulfone, sulfonate ester or sulphonamide group, a halogen such as fluorine, chlorine, bromine or iodine, —OH, —SH, —CN and —NO2, and/or combinations thereof.

The divalent linking groups $L^2$ and $L^3$ preferably independently represent an optionally substituted alkylene, cycloalkylene, arylene, or heteroarylene, —O, CO O, O—CO, CO NH, NH CO, NH CO O, O CO NH—, NH CO NH, NH CS NH, CO NR', NR" CO, NH CS NH, —SO—, —SO2-, —SO2-NH—, —NH—SO2-, —CH=N—, —NH—NH—, —N+(CH3)2-, —S—, —S—S—, and/or combinations thereof, wherein R' and R" each independently represent an optionally substituted alkyl, aryl, or heteroaryl. The substituents optionally present on the alkylene, the cyloalkylene, the arylene or the heteroarylene group may be represented by an alkyl group such as a methyl, ethyl, propyl or isopropyl group, substituents including for example oxygen or sulfur; a halogen such as a fluorine, chlorine, bromine or iodine atom; a hydroxyl group; an amino group; an alkoxy group such as a methoxy or ethoxy group or a (di)alkylamino group.

More preferably, the divalent linking groups $L^2$ and $L^3$ preferably independently represent a divalent aliphatic group including straight or branched carbon chain(s) or alicyclic, non-aromatic ring(s). Optionally the aliphatic linking group may contain substituents including for example oxygen or sulfur; alkyl groups such as a methyl, ethyl, propyl or isopropyl group and halogens such as a fluorine, chlorine, bromine or iodine atom.

Most preferably, the divalent linking groups $L^2$ and $L^3$ independently represent an optionally substituted alkylene or cycloalkylene group. The substituents optionally present on the alkylene or cycloalkylene group may be represented by an alkyl group such as a methyl, ethyl, propyl or isopropyl group or a halogen such as a fluorine, chlorine, bromine or iodine atom.

The amount of the compound according to the present invention in the overcoat layer is preferably between 10 and 98% wt, more preferably between 50 and 95% wt and most preferable between 60 and 90% wt, relative to the total amount of compounds in the overcoat layer. Alternatively, it is highly preferred that the level of inventive compound in the overcoat is between 10 and 500 mg/m$^2$, more preferably between 50 and 250 mg/m$^2$ and most preferably between 80 and 200 mg/m$^2$.

The overcoat layer preferably should be an efficient oxygen barrier layer which adheres sufficiently to the photopolymerisable layer or optional other layers of the coating. Besides acting as barrier for oxygen, the overcoat layer is preferably easily removable during processing and is sufficiently transparent for actinic radiation, e.g. from 300 to 450 nm or from 700 to 900 nm or from 750 to 1200 nm.

The overcoat layer can optionally contain any film-forming binder which is substantially transparent to the imaging radiation.

The overcoat layer preferably further comprises a water-soluble or water-swellable polymer or binder. Preferred binders which can be used in the top layer are disclosed in WO2005/029190 (page 36 line 3 to page 39 line 25), US 2007/0020563 (paragraph [0158]) and EP 1 288 720 (paragraphs [0148] and [0149]), including the cited references in these patents and patent applications. The overcoat layer may also contain a hydrophobic binder as disclosed in unpublished patent application EP18178933.

The most preferred optional binder for the toplayer is polyvinylalcohol and/or derivatives of polyvinyl alcohol. The polyvinylalcohol has preferably a hydrolysis degree ranging between 74 mol % and 99 mol %, more preferably between 88 mol % and 98 mol %. According to the present invention, it has been observed that combination of polyvinylalcohol which is not fully hydrolysed, e.g. polyvinylalcohol with a hydrolysis degree ranging between 85 mol % and 95 mol %, and the inventive compound, renders photopolymer printing plates having a good sensitivity while showing a decreased viscosity built up in the processing liquid. Combination with fully hydrolized polyvinylalcohol, i.e. polyvinylalcohol with a hydrolysis degree of about 98 mol %, may result in unwanted crystallization.

The weight average molecular weight of the polyvinylalcohol can be measured by the viscosity of an aqueous solution, 4% by weight, at 20° C. as defined in DIN 53 015, and this viscosity number ranges preferably between 3 and 26, more preferably between 3 and 15, most preferably between 3 and 10.

A mixture of polyvinylalcohols and/or other water-soluble polymers, or a mixture of polyvinylalcohols and/or derivatives of polyvinylalcohol having a different hydrolysis and viscosity number, may also be used, for example, a combination of two or more water-soluble polymers such as a combination of polyvinyl alcohol and polyvinylpyrrolidone. Modified polyvinylalcohols, e.g. polyvinylalcohols having a carboxyl group and/or a sulphonic acid group may also be used, preferably together with unmodified polyvinylalcohols.

The coating thickness of the overcoat layer is preferably between 0.10 and 1.75 g/m$^2$, more preferably between 0.20 and 1.30 g/m$^2$, most preferably between 0.25 and 1.0 g/m$^2$. In a more preferred embodiment of the present invention, the optional overcoat layer has a coating thickness between 0.30 and 0.50 g/m$^2$.

The overcoat layer may comprise other ingredients such as anionic surfactants, e.g. sodium alkyl sulphate or sodium alkyl sulphonate, sodium dioctylsulfosuccinate, sodium dodecylbenzenesulfonate, and ammoniumlaurylsulfate; amphoteric surfactants, e.g. alkylaminocarboxylate and alkylamino-dicarboxylate; non-ionic surfactants, e.g. polyethylene glycol, polypropylene glycol, and copolymer of ethylene glycol and propylene glycol, polysiloxane surfactants, perfluorocarbon surfactants, alkylphenyl ethylene oxide condensate, alkoxylated alkylene diamines disclosed in EP 1 085 380 (paragraph [0021] and [0022]), glycerine, inorganic particles, acids, pigments, etc. Various organic or inorganic micro particles may be added into the overcoat to, for example, reduce the tackiness or moisture sensitivity of the plate. The acid which is preferably water soluble and has a low molecular weight. Said acid may be an inorganic acid or an organic acid as disclosed in EP 2 149 071 page 27 lines 1 to 21. The overcoat layer may optionally include other ingredients such as matting agents or wetting agents as disclosed in EP 2 916 171 and are incorporated herein by reference.

The overcoat layer can be formed on the printing plate by coating a solution or dispersion, or by laminating a polymeric film. The coating can be performed by any known method, such as roller coating, slot coating, curtain coating, Mayer rod coating, dip coating, or spray coating; preferably roller coating or slot coating. The coated overcoat is further dried to remove the water and/or any solvent, preferably by forced hot air drying, radiation drying, or combination of forced air drying and radiation drying. The solution or dispersion containing a film-forming polymer suitable for forming the overcoat can be a water soluble polymer solution (containing water soluble polymer) or polymer dispersion (including polymer emulsion and latex, containing water-insoluble polymer, with or without addition of water soluble polymer), preferably a water soluble polymer solution. Various additives, such as further surfactants, wetting agents, defoamers, leveling agents and dispersing agents can be added to the overcoat to facilitate, for example, the coating and/or development process.

The polymeric film suitable for laminating onto the photosensitive layer to form the overcoat can be any polymeric film, such as polymer films based on polyester (including polyethylene terephthalate), polyethylene, polypropylene, ethylene/propylene copolymer, polystyrene, polyvinyl butyrol, polynitrile, polyamide, polyimide, polyvinyl chloride, polycarbonate, polymethylmethacrylate, acrylate/styrene copolymer, methacrylate/styrene copolymer, polyurethane, epoxy-amine polymer, nylon, Teflon, cellulose and its film forming derivatives, and polyvinyl acetate. Polyester, polyethylene and polypropylene are preferred polymeric film; and polyester is more preferred.

The overcoat is preferably removed during processing and/or on press with ink and/or fountain solution during on-press development.

The Lithographic Printing Plate Precursor

The lithographic printing plate precursor according to the present invention is negative-working, i.e. after exposure and development the non-exposed areas of the coating are removed from the support and define hydrophilic (non-printing) areas, whereas the exposed coating is not removed from the support and defines oleophilic (printing) areas. The hydrophilic areas are defined by the support which has a hydrophilic surface or is provided with a hydrophilic layer. The hydrophobic areas are defined by the coating, hardened upon exposing, optionally followed by a heating step. Areas having hydrophilic properties means areas having a higher affinity for an aqueous solution than for an oleophilic ink; areas having hydrophobic properties means areas having a higher affinity for an oleophilic ink than for an aqueous solution. "Hardened" means that the coating becomes insoluble or non-dispersible for the developing solution and may be achieved through polymerization and/or crosslinking of the photosensitive coating, which may be enhanced by the optional heating step.

Support

The lithographic printing plate used in the present invention comprises a support which has a hydrophilic surface or which is provided with a hydrophilic layer. The support is preferably a grained and anodized aluminium support, well known in the art. Suitable supports are for example disclosed in EP 1 843 203 (paragraphs [0066] to [0075]). The surface roughness, obtained after the graining step, is often expressed as arithmetical mean center-line roughness Ra (ISO 4287/1 or DIN 4762) and may vary between 0.05 and 1.5 μm. The aluminum substrate of the current invention has preferably an Ra value below 0.45 μm, more preferably below 0.40 μm and most preferably below 0.30 μm. The lower limit of the Ra value is preferably about 0.1 μm. More details concerning the preferred Ra values of the surface of the grained and anodized aluminum support are described in EP 1 356 926. By anodising the aluminum support, an $Al_2O_3$ layer is formed and the anodic weight (g/m$^2$ $Al_2O_3$ formed on the aluminum surface) varies between 1 and 8 g/m$^2$. The anodic weight is preferably; ≥3 g/m$^2$, more preferably ≥3.5 g/m$^2$ and most preferably ≥4.0 g/m$^2$.

The grained and anodized aluminum support may be subject to a so-called post-anodic treatment to improve the hydrophilic properties of its surface. For example, the aluminum support may be silicated by treating its surface with a sodium silicate solution at elevated temperature, e.g. 95° C. Alternatively, a phosphate treatment may be applied which involves treating the aluminum oxide surface with a phosphate solution that may further contain an inorganic fluoride. Further, the aluminum oxide surface may be rinsed with a citric acid or citrate solution. This treatment may be carried out at room temperature or may be carried out at a slightly elevated temperature of about 30 to 50° C. A further interesting treatment involves rinsing the aluminum oxide surface with a bicarbonate solution. Still further, the aluminum oxide surface may be treated with polyvinylphosphonic acid, polyvinylmethylphosphonic acid, phosphoric acid esters of polyvinyl alcohol, polyvinylsulphonic acid, polyvinylbenzenesulphonic acid, sulphuric acid esters of polyvinyl alcohol, and acetals of polyvinyl alcohols formed by reaction with a sulphonated aliphatic aldehyde.

Post treatment of the aluminum oxide surface with polyvinylphosphonic acid, polyvinylmethylphosphonic acid, phosphoric acid esters of polyvinyl alcohol, polyvinylsulphonic acid, polyvinylbenzenesulphonic acid, sulphuric acid esters of polyvinyl alcohol, and/or acetals of polyvinyl alcohols formed by reaction with a sulphonated aliphatic aldehyde, is especially preferred. More preferred is post treatment of the aluminum oxide surface with polyvinylphosphonic acid, polyvinylmethylphosphonic acid, phosphoric acid esters of polyvinyl alcohol and/or polyvinylsulphonic acid. Most preferred is the treatment of the aluminum oxide surface with polyvinylphosphonic acid.

Another useful post-anodic treatment may be carried out with a solution of polyacrylic acid or a polymer comprising at least 30 mol % of acrylic acid monomeric units, e.g. GLASCOL E15, a polyacrylic acid, commercially available from Ciba Speciality Chemicals.

Alternatively, the support may be treated with an adhesion promoting compound such as those described in EP 1 788 434 in [0010] and in WO 2013/182328.

Besides an aluminium support, a plastic support, for example a polyester support, provided with one or more hydrophilic layers as disclosed in for example EP 1 025 992 may also be used.

Photopolymer Coating

The coating has, besides the overcoat layer, at least one layer including a photopolymerisable composition, said layer is also referred to as the "photopolymeisable layer". The photopolymerisable layer preferably has a coating thickness preferably ranging between 0.2 and 5.0 g/m$^2$, more preferably between 0.4 and 3.0 g/m$^2$, most preferably between 0.6 and 2.2 g/m$^2$. The coating may, besides the overcoat layer described above, include other layers such as for example an adhesion-improving layer, located between the support and the photopolymerisable layer.

The photopolymerisable composition preferably includes a polymerisable compound. The polymerisable compound may be a monomer or oligomer including at least one epoxy or vinyl ether functional group and the polymerisation initiator is a Brönsted acid generator capable of generating free acid, optionally in the presence of a sensitizer. Suitable polyfunctional epoxy monomers and suitable Brönsted acid generators are disclosed in WO2014/198820 [048] and [049].

The polymerisable compound is most preferably a polymerisable monomer or oligomer including at least one terminal ethylenic group, hereinafter also referred to as "free-radical polymerisable monomer". The polymerisation involves the linking together of the free-radical polymerisable monomers.

Suitable free-radical polymerisable monomers are disclosed in [0050] and [0051] of WO2014/198820 and are incorporated herein by reference.

Initiator

In a highly preferred embodiment, the coating—preferably the photopolymerisable layer—preferably contains a free radical initiator capable of generating free radicals upon exposure directly or in the presence of a sensitizer. Suitable free-radical initiators are described in WO 2005/111727 from page 15 line 17 to page 16 line 11 and EP 1 091 247 and may include for example hexaaryl-bisimidazole compound (HABI; dimer of triaryl-imidazole), aromatic ketones, aromatic onium salts, organic peroxides, thio compounds, keto-oxime ester compounds, borate compounds, azinium compounds, metallocene compounds, active ester compounds and further compounds having a carbon-halogen bond.

The coating, preferably the photopolymerisable layer, may also comprise a co-initiator. Typically, a co-initiator is used in combination with a free radical initiator. Suitable co-initiators for use in the photopolymer coating are disclosed in U.S. Pat. Nos. 6,410,205; 5,049,479; EP 1 079 276, EP 1 369 232, EP 1 369 231, EP 1 341 040, US 2003/0124460, EP 1 241 002, EP 1 288 720 and in the reference book including the cited references: Chemistry & Technology UV & EB formulation for coatings, inks & paints—Volume 3—Photoinitiators for Free Radical and Cationic Polymerisation by K. K. Dietliker—Edited by P. K. T. Oldring—1991—ISBN 0 947798161. Specific co-initiators, as described in EP 107 792, may be present in the photopolymerisable layer to further increase the sensitivity. Preferred co-initiators are disclosed in EP 2 916 171 [0051] and are incorporated herein by reference.

A very high sensitivity can be obtained by including a sensitizer such as for example an optical brightener in the coating. Suitable examples of optical brighteners as sensitizers are described in WO 2005/109103 page 24, line 20 to page 39. Other preferred sensitizers are blue, green or red light absorbing sensitizers, having an absorption spectrum between 450 nm and 750 nm. Useful sensitizers can be selected from the sensitizing dyes disclosed in U.S. Pat. Nos. 6,410,205; 5,049,479; EP 1 079 276, EP 1 369 232, EP 1 369 231, EP 1 341 040, US 2003/0124460, EP 1 241 002 and EP 1 288 720.

Infrared Absorbing Compound

In another preferred embodiment, the coating may include an infrared absorbing compound. The IR absorbing compound may be an infrared light absorbing dye or pigment. An infrared light absorbing dye is preferred, also referred to herein as IR-dye. The infrared light absorbing dye preferably has an absorption spectrum between 750 nm and 1500 nm, preferably between 780 nm and 1200 nm, more preferably between 800 nm and 1100 nm. The IR absorbing compound absorbs infrared light and converts the absorbed energy into heat.

The concentration of the IR-dyes with respect to the total dry weight of the coating, is preferably from 0.25 wt % to 25.0 wt %, more preferably from 0.5 wt % to 20.0 wt %, most preferred from 1.0 wt % to 10.0 wt %.

The infrared absorbing compound is preferably present in the photopolymerisable layer; but may also be present in the overcoat layer and/or in an optional other layer. Preferred IR absorbing compounds are dyes such as cyanine, merocyanine, indoaniline, oxonol, pyrilium and squarilium dyes or pigments such as carbon black. Examples of suitable IR absorbers are described in e.g. EP 823 327, EP 978 376, EP 1 029 667, EP 1 053 868, EP 1 093 934; WO 97/39894 and WO 00/29214. Particular preferred dyes are heptamethinecyane dyes, especially the dyes disclosed in EP 1 359 008 paragraph [0030] to [0032].

Binder

The coating preferably includes a binder, preferably, the binder is present in the photopolymerisable layer. The binder can be selected from a wide series of organic polymers. Compositions of different binders can also be used. Useful binders are described in WO2005/111727 page 17 line 21 to page 19 line 30, EP 1 043 627 in paragraph [0013] and in WO20051029187 page 16 line 26 to page 18 line 11. Suitable binders include hydrophilic binders such as homopolymers and copolymers of vinyl alcohol, acrylamide, methylol acrylamide, methylol methacrylamide, acrylic acid, methacrylic acid, hydroxyethyl acrylate, hydroxyethyl methacrylate and maleic anhydride/vinylmethylether copolymers.

Other Ingredients

Optionally, the coating may further contain additional ingredients. These ingredients may be present in the photopolymerisable layer, in the overcoat layer or in an optional other layer.

For example, the photopolymerisable layer may also comprise particles which increase the resistance of the coating against manual or mechanical damage. The particles may be inorganic particles, organic particles or fillers such as described in for example U.S. Pat. No. 7,108,956. More details of suitable spacer particles described in EP 2 916 171 [0053] to [0056] are incorporated herein by reference.

The photopolymerisable layer may also comprise an inhibitor. Particular inhibitors for use in the photopolymer coating are disclosed in U.S. Pat. No. 6,410,205, EP 1 288 720 and EP 1 749 240.

The photopolymerisable layer may further comprise an adhesion promoting compound which may improve the adhesion between the coating and the support and the durability of the plate in the printing process. The adhesion promoting compound is a compound capable of interacting with the support, preferably a compound having an addition-polymerizable ethylenically unsaturated bond and a functional group capable of interacting with the support; for example a phosphate group, a phosphonate group and a tialkoxysilane group. The compound can be present in the photopolymerisable layer or in an intermediate layer between the support and the photopolymerisable layer. Suitable examples thereof are disclosed in EP 1 788 434 in [0010], WO 2013/182328, EP 851 299, EP 1 091 251, US 2004/214105, EP 1 491 356, US 2005/39620, EP 1 495 866, EP 1 500 498, EP 1 520 694 and EP 1 557 262, EP 2 212 746 and EP 2007/059379.

Various surfactants may be added into the photopolymerisable layer to allow or enhance the developability of the precursor; especially developing with a gum solution. Both polymeric and small molecule surfactants for example non-ionic surfactants are preferred. More details are described in EP 2 916 171 [0059] and are incorporated herein by reference.

Preferably the coating includes a printing-out agent, i.e. a compound which is capable of changing the color of the coating upon exposure. After image-wise exposing the precursor, a visible image can be produced, also referred to as "print-out image". The printing-out agent may be a compound as described in EP-A-1 491 356 paragraph [0116] to [0119] on page 19 and 20, and in US 2005/008971 paragraph [0168] to [0172] on page 17. Preferred printing-out agents are the compounds described in EP 1 765 592 from line 1 page 9 to line 27 page 20. More preferred are the IR-dyes as described in EP 1 736 312 from line 32 page 5 to line 9 page 32. The contrast of the image formed after image-wise exposure (and processing) enables the end-user to establish immediately whether or not the precursor has already been exposed (and processed), to distinguish the different color selections and to inspect the quality of the image on the plate precursor. In order to obtain a good visual contrast for a human observer the type of color of the colorant may also be important. Preferred colors for the colorant are cyan or blue colors, i.e. under blue color we understand a color that appears blue for the human eye.

Method for Making a Lithographic Printing Plate Precursor

According to the present invention there is also provided a method for making a negative-working lithographic printing plate comprising the steps of imagewise exposing the printing plate precursor of the present invention followed by developing the imagewise exposed precursor so that the non-exposed areas are dissolved in the developer solution. The lithographic printing plate precursor can be prepared by (i) applying on a support as described above the coating as described above and (ii) drying the precursor.

Exposure Step

The printing plate precursor is preferably exposed to laser light. Preferably, the image-wise exposing step is carried out off-press in a platesetter, i.e. an exposure apparatus suitable for image-wise exposing the precursor with a laser such as a laser diode, emitting around 830 nm, a Nd YAG laser, emitting around 1060 nm, a violet laser, emitting around 400 nm, or a gas laser such as an Ar laser, or with a digitally modulated UV-exposure set-up, using e.g. digital mirror devices, or by a conventional exposure in contact with a mask. Preferably, the precursor is image-wise exposed by a laser emitting IR-light (i.e. wavelengths ranging between 750 and 1500 nm) or violet light (i.e. wavelengths ranging between 350 and 450 nm); most preferred by a laser emitting IR-light.

Preheat Step

After the exposing step, the precursor may be pre-heated whereby the polymerization and/or crosslinking reaction of the photopolymerisation layer may be enhanced. The heating is preferably at a temperature between 80° C. and 300° C. more preferably between 100° C. and 250° C. and most preferably between 120° and 200° C. The applied period of this heat; i.e. the dwell time, is preferably between 2 s and 30 minutes, more preferably between 10 s and 15 minutes and most preferably between 15 s and 10 minutes. This heating step may be performed in a preheating unit comprising a heating element such as for example an IR-lamp, an UV-lamp, heated air or a heated roll.

Development Step

Subsequently to the exposing step and the optional preheat step, the plate precursor may be processed. Before developing the imaged precursor, a pre-rinse step might be carried out to remove, at least partly, the overcoat layer. This pre-rinse step can be carried out in a stand-alone apparatus or by manually rinsing the imaged precursor with water or the pre-rinse step can be carried out in a washing unit that is integrated in a processor used for developing the imaged precursor. The washing liquid is preferably water, more preferably tap water. More details concerning the wash step are described in EP 1 788 434 in [0026].

During the development step, the non-exposed areas of the image-recording layer are at least partially removed without essentially removing the exposed areas. The processing liquid, also referred to as developer, can be applied to the plate e.g. by rubbing with an impregnated pad, by dipping, immersing, coating, spincoating, spraying, pouring-on, either by hand or in an automatic processing apparatus. The treatment with a processing liquid may be combined with mechanical rubbing, e.g. by a rotating brush. During the development step, any water-soluble protective layer present is preferably also removed. The development is preferably carried out at temperatures between 20 and 40° C. in automated processing units.

In a highly preferred embodiment, the processing step as described above is replaced by an on-press processing whereby the imaged precursor is mounted on a press and processed on-press by rotating said plate cylinder while feeding dampening liquid and/or ink to the coating of the precursor to remove the unexposed areas from the support.

The processing step may also be performed by combining embodiments described above, e.g. combining development with a processing liquid with development on-press by applying ink and/or fountain.

Processing Liquid

The processing liquid may be an alkaline developer or solvent-based developer. Suitable alkaline developers have been described in US2005/0162505. An alkaline developer is an aqueous solution which has a pH of at least 11, more typically at least 12, preferably from 12 to 14. Alkaline developers typically contain alkaline agents to obtain high pH values can be inorganic or organic alkaline agents. The developers can comprise anionic, non-ionic and amphoteric surfactants (up to 3% on the total composition weight); biocides (antimicrobial and/or antifungal agents), antifoaming agents or chelating agents (such as alkali gluconates), and thickening agents (water soluble or water dispersible polyhydroxy compounds such as glycerine or polyethylene glycol).

Preferably, the processing liquid is a gum solution whereby during the development step the non-exposed areas of the photopolymerisable layer are removed from the support and the plate is gummed in a single step. The development with a gum solution has the additional benefit that, due to the remaining gum on the plate in the non-exposed areas, an additional gumming step is not required to protect the surface of the support in the non-printing areas. As a result, the precursor is processed and gummed in one single step which involves a less complex developing apparatus than a developing apparatus comprising a developer tank, a rinsing section and a gumming section. The gumming section may comprise at least one gumming unit or may comprise two or more gumming units. These gumming units may have the configuration of a cascade system, i.e. the gum solution, used in the second gumming unit and present in the second tank, overflows from the second tank to the first tank when gum replenishing solution is added in the second gumming unit or when the gum solution in the second gumming unit is used once-only, i.e. only starting gum solution is used to develop the precursor in this second gumming unit by preferably a spraying or jetting technique. More details concerning such gum development is described in EP1 788 444.

A gum solution is typically an aqueous liquid which comprises one or more surface protective compounds that are capable of protecting the lithographic image of a printing plate against contamination, e.g. by oxidation, fingerprints, fats, oils or dust, or damaging, e.g. by scratches during handling of the plate. Suitable examples of such surface protective compounds are film-forming hydrophilic polymers or surfactants. The layer that remains on the plate after treatment with the gum solution preferably comprises between 0.005 and 20 g/m² of the surface protective compound, more preferably between 0.010 and 10 g/m², most preferably between 0.020 and 5 g/m². More details concerning the surface protective compounds in the gum solution can be found in WO 2007/057348 page 9 line 3 to page 11 line 6. As the developed plate precursor is developed and gummed in one step, there is no need to post-treat the processed plate.

The gum solution preferably has a pH value between 3 and 11, more preferably between 4 and 10, even more preferably between 5 and 9, and most preferably between 6 and 8. A suitable gum solution is described in for example EP 1 342 568 in [0008] to [0022] and WO2005/111727. The gum solution may further comprise an inorganic salt, an anionic surfactant, a wetting agent, a chelate compound, an antiseptic compound, an anti-foaming compound and/or an ink receptivity agent and/or combinations thereof. More details about these additional ingredients are described in WO 2007/057348 page 11 line 22 to page 14 line 19.

Drying and Baking Step

After the processing step the plate may be dried in a drying unit. In a preferred embodiment the plate is dried by heating the plate in the drying unit which may contain at least one heating element selected from an IR-lamp, an UV-lamp, a heated metal roller or heated air.

After drying the plate can optionally be heated in a baking unit. More details concerning the heating in a baking unit can be found in WO 2007/057348 page 44 line 26 to page 45 line 20.

The printing plate thus obtained can be used for conventional, so-called wet offset printing, in which ink and an aqueous dampening liquid is supplied to the plate. Another suitable printing method uses a so-called single-fluid ink without a dampening liquid. Suitable single-fluid inks have been described in U.S. Pat. Nos. 4,045,232; 4,981,517 and 6,140,392. In a most preferred embodiment, the single-fluid ink comprises an ink phase, also called the hydrophobic or oleophilic phase, and a polyol phase as described in WO 00/32705.

EXAMPLES

Example 1

1. Synthesis of the Inventive Compounds.

The structure of the inventive compounds INV-01 to INV-06 which were prepared following the experimental procedures given below are given in Table 1.

2. Experimental Procedure

Synthesis of N,N'-bis[2-(2-hydroxyethoxy)ethyl]oxamide—INV-01

Reagent—01

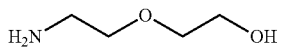

To a solution of diethyloxalate (221.4 g, 1.50 mol, 1 equl.) in 325 mL EtOH under N2 was added Reagent 01 (2-(2-Aminoethoxy)ethanol, 338 g, 3.15 mol, 2.1 equi.) over 25 minutes via a dropping addition funnel under N2. The addition funnel was further rinsed with 45 ml EtOH before the reaction mixture was stirred for 1 h at 55° C.; the colorless mixture turned light yellow. An additional 125 ml EtOH was added to the mixture, and the stirring was continued for 20 min at 55° C. Subsequently, 250 mL of a 3/1 MTBE/Acetone mixture was added in one portion, and the reaction mixture was kept under vigorous stirring at the same temperature for 45 min prior to slow cooling to room temperature. An additional 750 mL of a 3/1 MTBE/Acetone mixture was then added in one portion, under stirring. The crude precipitate was then filtered off and the solid washed with 180 mL of a 3/1 MTBE/Acetone mixture. The solid was then re-dispersed in 700 mL of a 3/1 MTBE/Acetone mixture. A second filtration was carried out, followed by a washing step of the solid using 300 ml of a 3/1 MTBE/Acetone mixture. The white solid was collected and placed in a ventilated dry oven at 50° C. overnight until complete evaporation of the solvents.

Yield: 84%

Synthesis of N,N'-bis(3-hydroxypropyl)oxamide—INV-02

Reagent 02

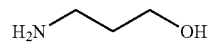

To a solution of diethyloxalate (100.0 g, 0.68 mol, 1 equl.) in 500 mL EtOH was added Reagent 02 (3-aminopropan-1-ol, 102.1 g, 1.36 mol, 2 equl.) in solution in 160 mL EtOH over 10 minutes via a dropping addition funnel. After addition, stirring is continued for 1 h at r.t. The crude mixture was warmed up to 35° C. prior to the filtration of the white precipitate. The mother liquor was reserved for a further 72 h crystallization of a white solid. The 2 solids were mixed and dried in a dry oven at 40° C., overnight. Then, a second drying step under vacuum took place.

Yield: 85%

Synthesis of N,N'-bis(2-hydroxy-1-methyl-ethyl)oxamide—INV-03

Reagent 03

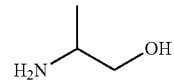

To a solution of diethyloxalate (11.1 g, 0.075 mol, 1 equi.) in 18 mL EtOH under N2 was added Reagent 03 (2-aminopropan-1-ol, 11.9 g, 0.158 mol, 2.1 equi.) in solution in 45 mL MTBE under N2, over 8 minutes via a dropping addition funnel. The addition funnel was further rinsed with 5 mL EtOH. After addition, stirring is continued for 40 min at r.t. The crude mixture contains a white precipitate which was filtered off and washed twice with a 3/1 MTBE/Acetone mixture. The white solid was dried in a dry oven at 40° C., overnight. Then, a second drying step under vacuum took place.

Yield: 84%

Synthesis of N,N'-bis(1,2-dihydroxyethyl)oxamide—INV-04

Reagent 04

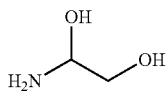

Reagent 04 (1-aminoethane-1,2-diol, 11.7 g, 0.126 mol, 2.1 equi.) was dissolved in a solvent mixture of 30 mL EtOH and 36 mL MTBE under N2. To this solution was added diethyloxalate (11.1 g, 0.075 mol, 1 equi.) under N2, over 5 minutes via a dropping addition funnel. After addition, stirring is continued for 40 min at r.t. The crude mixture contains a white precipitate which was filtered off and washed twice with a 3/1 MTBE/Acetone mixture. The white solid was dried in a dry oven at 40° C., overnight. Then, a second drying step under vacuum took place.

Yield: 90%

Synthesis of N,N'-bis(2-hydroxyphenyl)oxamide—INV-05

Reagent 05

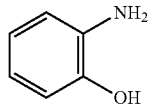

NaHCO$_3$ (18.0 g, 0.21 mol, 1.05 equi.) was suspended in a solution of Reagent 05 (21.8 g, 0.20 mol, 1.00 equi.) in 150 mL CH$_2$Cl$_2$. 25 mL DMA and pyridine (15.8 g, 0.20 mol, 1.00 equi) were added to the suspension prior to cooling it to −2° C. A solution of oxalyl chloride (11.4 g, 0.09 mol, 0.45 equi) in 25 mL CH$_2$Cl$_2$ was added to the suspension, the temperature of the reaction mixture being kept below 5° C. during the course of the addition. The orange suspension was stirred for an additional 30 minutes at 5° C., then warmed up to 15° C. CH$_2$Cl$_2$ was evaporated. 200 mL HCl 1N was added to the residual concentrated suspension under stirring, prior to filtration. The solid was washed with water and further digested in refluxing MeOH. The suspension was filtered off and the solid was further purified by preparative chromatography on (Amicon 35-70, column diameter 8 cm, column length 45 cm, eluent CH$_2$Cl$_2$/MeOH 95/5, debit 90 mL/min; pressure 3 Kg/cm$^2$) followed by solvent evaporation and drying in a ventilated dry oven at 40° C., overnight.

Yield: 20%

Synthesis of N,N'-bis(2-hydroxyethyl)oxamide—INV-06

Reagent 06

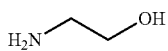

To a solution of dimethyloxalate (119 g, 1 mol, 1 equi.) in 840 mL MeOH at 18° C. and under N2 flow was added Reagent 06 (2-aminoethanol, 130 g, 2.1 mol, 2.1 equi.) over 90 minutes via a dropping addition funnel. After addition, stirring is continued for 40 min at 18° C. The crude mixture contained a white precipitate which was filtered off and washed three times with 200 mL MeOH. The white solid was dried in a dry oven at 70° C., prior to recrystallization in 2 L refluxing MeOH and further filtration. The collected white solid was recrystallized in 500 mL refluxing MeOH and further filtered off. The white solid was dried in a dry oven at 70° C.

Yield: 68%

TABLE 1

Inventive compounds INV-01 to INV-06

| Compound | Structure |
|---|---|
| INV-01 | 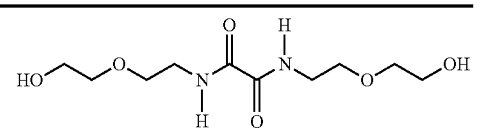 |
| INV-02 | 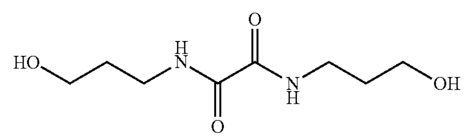 [SMILES: O=C(NCCCO)C(=O)NCCCO] |
| INV-03 | 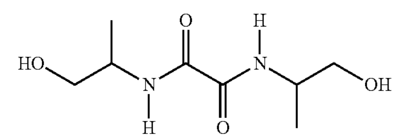 |
| INV-04 | 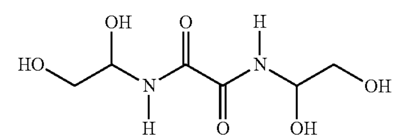 [SMILES: O=C(NC(O)CO)C(=O)NC(O)CO] |
| INV-05 | 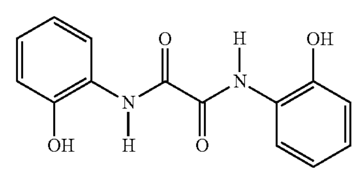 [SMILES: O=C(Nc1ccccc1O)C(=O)Nc1ccccc1O] |
| INV-06 | 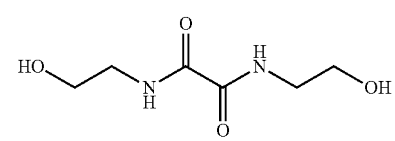 [SMILES: O=C(NCCO)C(=O)NCCO] |

1. Preparation of the Lithographic Support S-01

A 0.3 mm thick aluminium foil was degreased by spraying with an aqueous solution containing 26 g/l NaOH at 65° C. for 2 seconds and rinsed with demineralised water for 1.5 seconds. The foil was then electrochemically grained during 10 seconds using an alternating current in an aqueous solution containing 15 g/l HCl, 15 g/l SO$_4^{2-}$ ions and 5 g/l Al$^{3+}$ ions at a temperature of 37° C. and a current density of about 100 A/dm$^2$. Afterwards, the aluminium foil was then desmutted by etching with an aqueous solution containing 5.5 g/l of NaOH at 36° C. for 2 seconds and rinsed with demineralised water for 2 seconds. The foil was subsequently subjected to anodic oxidation during 15 seconds in an aqueous solution containing 145 g/l of sulfuric acid at a temperature of 50° C. and a current density of 17 A/dm$^2$, then washed with demineralised water for 11 seconds and dried at 120° C. for 5 seconds.

The support thus obtained was characterised by a surface roughness Ra of 0.35-0.4 μm (measured with interferometer NT1100) and had an anodic weight of 3.0 g/m².

2. Preparation of the Printing Plate Precursors PP-01 to PP-07

Photosensitive Layer

The printing plate precursors were produced by coating onto the above described support S-01, the photopolymerisable layer PL-01 or PL-02 as defined in Table 2 dissolved in a mixture of 35% by volume of MEK and 65% by volume of Dowanol PM (1-methoxy-2-propanol, commercially available from DOW CHEMICAL Company). The coating solutions PL-01 and PL-02 were applied at a wet coating thickness of 30 μm and then dried at 120° C. for 1 minute in a circulation oven.

TABLE 2

| | dry coating weight of the photosensitive layers PL-01 and PL-02 | |
|---|---|---|
| Ingredients (Dry weight) | PL-01 mg/m² | PL-02 mg/m² |
| IR dye-01 (1) | 22 | — |
| UV dye (1) | — | 106 |
| Binder-01 (2) | 150 | — |
| Binder-02 (2) | — | 140 |
| FST 426R (3) | 270 | 300 |
| CN 104 (4) | 320 | — |
| SR368 (5) | — | 300 |
| Ini-01 (6) | 30 | — |
| Ini-02 (6) | — | 128 |
| Ini-03 (6) | — | 14 |
| Tegoglide 410 (7) | 1.5 | 2.1 |
| Sipomer PAM 100 (8) | 130 | 180 |
| Pig-disp (9) | 120 | 90 |

(1) IR dye-01 is an infrared absorbing dye commercially available from FEW Chemicals as S2025 having the following structure:

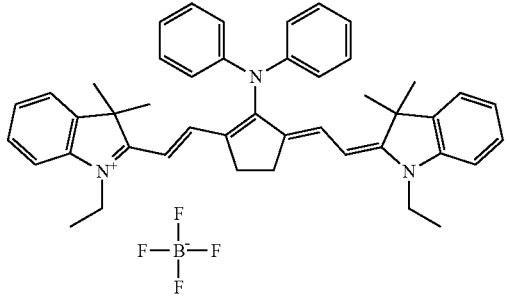

UV dye is 1,4-di[3,5-dimethoxy, 4-isobutoxy-styrylbenzene

IR dye-02 is an infrared absorbing dye commercially available from Hampford Research Inc. as IR dye 813 having the following structure:

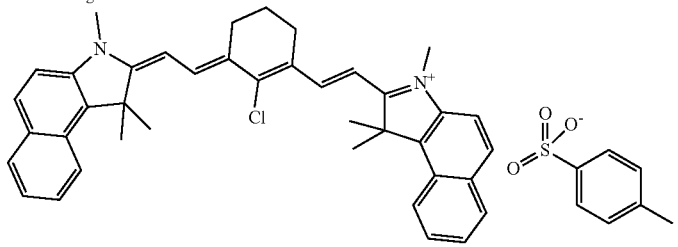

(2) Binder-01 represents Ruco Coat EC4811, an aliphatic polyether polyurethane commercially available as a 30 wt. % aqueous dispersion from Rudolf GmbH;
Binder-02 represents S-LEC BX35Z, a polyvinyl butyral commercially available from Sekisui;

(3) FST 510 is a reaction product from 1 mole of 2,2,4-trimethylhexamethylenediisocyanate and 2 moles of hydroxyethyl-methacrylate commercially available from AZ Electronics as an 82 wt. % solution in MEK;

(4) CN 104 is bisphenol A epoxy diacrylate commercially available from Arkema;

(5) SR368 is a triacrylate modified isocyanuric acid commercially available from Arkema;

(6) Ini-01 is Bis(4-tert-butyl phenyl) iodonium tetraphenylborate is an onium initiator commercially available from AZ electronics;
Ini-02 is 2,2'-bis(2-chlorophenyl)-4,4',5,5'-tetraphenyl-1,2-bisimidazole;
Ini-03 is 2-mercaptobenzothiazole;

(7) Tegoglide 410 is a surfactant commercially available from Evonik Tego Chemie GmbH;

(8) Sipomer PAM 100 is a methacrylate phosphonic ester commercially available from Rhodia;

(9) Pig-disp is 30 wt. % dispersion in Dowanol PM made from 20 wt. % pigment blue 60 (commercially available from Dominion Color Corporation) stabilized with 10 wt. % bykjet 9152 (commercially available from Byk).

Overcoat Layer

On top of the photosensitive layer, an aqueous solution including the composition as defined in Table 3 was coated (40 μm wet thickness) and dried at 120° C. for 2 minutes. The compositions of the different top layers are defined in Table 3.

TABLE 3

Composition of the overcoats OC-01 to OC-04

| INGREDIENT | OC-1 | OC-2 | OC-3 | OC-4 g | OC-5 | OC-6 |
|---|---|---|---|---|---|---|
| Mowiol 4-88 (1) | 15.1 | 15.1 | 7.6 | — | — | 24.2 |
| Mowiol 4-98 (1) | 9.1 | — | — | 9.1 | — | — |
| Lutensol A8 (2) | 0.27 | 0.27 | 0.14 | 0.27 | 0.27 | 0.27 |
| INV-1 (3) | — | 9.1 | 4.6 | 15.1 | 24.2 | — |
| Water | 975 | 975 | 986 | 975 | 975 | 975 |

(1) Mowiol 4-88 ™ is partially hydrolyzed polyvinyl alcohols commercially available from Kuraray; Mowiol 4-98 ™ is a fully hydrolysed polyvinylalcohol, commercially available from Kuraray;
(2) Lutensol A8 ™ is a surface active agent commercially available from BASF;
(3) INV-1 is the inventive compound according to the following formula:

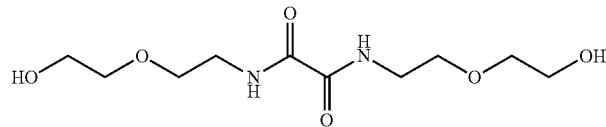 [SMILES: O=C(NCCOCCO)C(=O)NCCOCCO]

The printing plate precursors PPP-01 to PPP-07 were obtained. Table 4 gives an overview of the inventive and comparative printing plate precursors PPP-01 to PPP-07.

TABLE 4

Overview of the printing plate precursors PPP-01 to PPP-07

| Printing plate precursor | Coating Composition | Overcoat |
|---|---|---|
| PPP-01 Inventive | PL-01 | OC-02 |
| PPP-02 Inventive | PL-01 | OC-03 |
| PPP-03 Comparative | PL-01 | OC-01 |
| PPP-04 Comparative | PL-01 | OC-06 |
| PPP-05 Inventive | PL-02 | OC-04 |
| PPP-06 Inventive | PL-02 | OC-05 |
| PPP-07 Comparative | PL-02 | OC-01 |

3. Imaging

The printing plate precursors PPP-01 to PPP-04 were imaged at 2400 dpi with a High Power Creo 40W TE38 thermal platesetter (200 lpi Agfa Balanced Screening (ABS)), commercially available from Kodak and equipped with a 830 nm IR laser diode, at energy densities between 60 and 120 mJ/cm2.

The printing plate precursors PPP-5 to PPP-7 were imaged at 1270 dpi with a violet platesetter device (flat bed system, Polaris) equipped with a violet laser diode emitting between 392 to 417 nm (variable image plane power from 0 to 10.5 mW with a scanning speed of 1000 m/s) at an energy density of 80 μJ/cm2.

4. Development

The printing plate precursors PPP-01 to PPP-07 were processed with Violet CF GUM-NP™ commercially available from Agfa Graphics NV in an Azura C95 Processor™ (Speed 60 cm/min, at 20° C.), available from Agfa Graphics NV, to remove the coating in the non-image areas from the support. The obtained plates were dried with hot air at 50° C. Printing plates PP-01 to PP-07 were obtained.

Additionally, un-exposed printing plate precursors (1.5 m2) were developed with Violet CF GUM-NP™ in a volume of 100 ml to evaluate the viscosity increase. During exhaustion, development chemistry consumption is limited by viscosity increases due to dissolution of the hydrophilic top coat polymer(s). 5. Results Sensitivity After image-wise exposure and development, the dot rendering on the printing plates PP-01 to PP-07 was evaluated with a 50× magnification hand microscope and measured with a Techkon SpectroPlate™; commercially available from Techkon. The sensitivity was defined as the exposure energy needed to obtain a minimal dot gain (the difference between the measured dot coverage and the digital value) of 3% for a 40% 200 lpi ABS dot rendering. The results of the sensitivity test are summarized in Table 5 below.

All printing plates have a good sensitivity and the results in Table 5 demonstrate the feasibility of reducing the fraction of polyvinyl alcohol from the protective layer and/or addition of the inventive compound, without impairing the plate sensitivity.

The sensitivity of inventive printing plate P-06 including no polyvinyl alcohol rendered a less sensitive plate compared to the other printing plates including polyvinyl alcohol.

Viscosity 1.5 m² of an un-exposed printing plate precursor was developed with 100 ml of Violet CF GUM-NP™. The dissolution of the hydrophilic polymers in the overcoat layer during development results in a viscosity increase of the gum solution. The viscosity increase of the gum solution was determined using calibrated pipets commercially available from LSB (Labo Service Belgium glass technology). Pipets are calibrated to be suitable in a targeted kinematic viscosity range. The gum solutions were loaded in the calibrated pipet at 25° C. and the time needed for the level of the fluid to pass between the calibration marks is proportional to the kinematic viscosity. By multiplying this time taken by the factor of the viscosimeter, the kinematic viscosity is obtained. The difference with the measured kinematic viscosity of the starting gum liquid gives the viscosity increase.

The results clearly demonstrate that the viscosity increase of the processing liquid is significantly lower for inventive printing plates PP-01, PP-02, PP-05 and PP-06 compared to the comparative printing plates PP-03, PP-04 and PP-07. PP-06 including no polyvinyl alcohol in the overcoat layer, shows the lowest viscosity increase. The viscosity increase can be attributed to the presence of polyvinyl alcohol. The results of the viscosity test are summarized in Table 5 below.

TABLE 5

Results of the Sensitivity and the Viscosity increase of printing plates PP-01 to PP-07

| Printing plate | Sensitivity* mJ/cm2 | Viscosity increase* cP |
|---|---|---|
| PP-01 Inventive | 77 | 8.1 |
| PP-02 Inventive | 88 | 3.4 |
| PP-03 Comparative | 65 | 18.2 |
| PP-04 Comparative | 85 | 17.8 |
| PP-05 Inventive | 85 | 3.8 |
| PP-06 Inventive | >100 | 1.8 |
| PP-07 Comparative | 80 | 18.4 |

*See above

The printing plates PP-05 and PP-07 were mounted on a Heidelberg GTO 46 printing press. Each print job was started using K+E Novavit 800 Skinnex ink (trademark of BASF Druckfarben GmbH) mixed with 0.5% wt sodium carbonate and 4 wt % Prima FS404 (trademark of Agfa Graphics) in water as fountain solution. A compressible blanket was used and printing was performed on non-coated offset paper. The dot loss of the 40% 200 lpi ABS (Agfa Balanced screening, commercially available from Agfa Graphics N.V.), the 40% sublime 240 screening, and the B25 2% screening were evaluated after 30,000 printed sheets. All prints were performed on double sided matt coated (90 g) paper.

Inventive printing plate PP-05 rendered similar dot gain on print compared to comparative printing plate PP-07.

Example 2

1. Preparation of the Printing Plate Precursors PP-08 to PP-10

Photosensitive Layer

The photopolymerisable layer PL-04 was prepared by coating onto the above described support S-01 the components as defined in Table 6 dissolved in a mixture of 35% by volume of MEK and 65% by volume of Dowanol PM (1-methoxy-2-propanol, commercially available from DOW CHEMICAL Company). The coating solution was applied at a wet coating thickness of 30 μm and then dried at 120° C. for 1 minute in a circulation oven.

TABLE 6

Photosensitive layer PL-04

| INGREDIENTS* | PL-04 mg/m² |
|---|---|
| IR-dye-02 | 22 |
| Binder-03 | 150 |

TABLE 6-continued

Photosensitive layer PL-04

| INGREDIENTS* | PL-04 mg/m² |
|---|---|
| Ebecryl 220 | 450 |
| Mono Z | 150 |
| Ini-01 | 60 |
| Tegoglide 410 | 1.5 |
| Sipomer PAM 100 | 130 |

*See Table 2 above

Overcoat Layer

On top of the photosensitive layer, an aqueous solution including the composition as defined in Table 7 was coated (40 μm wet thickness) and dried at 120° C. for 2 minutes. The compositions of the different top layers are defined in Table 7.

TABLE 7 composition of the overcoat layers OC-01, OC-07 to OC-08

| INGREDIENT* | OC-1 g | OC-7 g | OC-8 g |
|---|---|---|---|
| Mowiol 4-88 (1) | 15.1 | 19.37 | 19.37 |
| Mowiol 4-98 (1) | 9.1 | 11.68 | 11.68 |
| Lutensol A8 (2) | 0.27 | 0.30 | 0.30 |
| INV-1 (3) | — | 0.32 | 3.21 |
| Water | 975 | 966.7 | 963.8 |

*See Table 3 above

2. Preparation of the Printing Plate Precursors PP-08 to PP-10

The printing plate precursors PPP-08 to PPP-10 were obtained. Table 8 gives an overview of the inventive and comparative printing plate precursors PPP-08 to PPP-10.

TABLE 8

Overview of the printing plate precursors PPP-08 to PPP-10

| Printing plate precursor | Coating Composition | Overcoat |
|---|---|---|
| PPP-08 Comparative | PL-04 | OC-01 |
| PPP-09 Inventive | PL-04 | OC-07 |
| PPP-10 Inventive | PL-04 | OC-08 |

3. Imaging

The printing plate precursors PPP-08 to PPP-10 were imaged at 2400 dpi with a High Power Creo 40W TE38 thermal platesetter (200 lpi Agfa Balanced Screening (ABS)), commercially available from Kodak and equipped with a 830 nm IR laser diode, at an energy density of 80 mJ/cm².

4. On Press Development

After imaging, the plate precursors PPP-8 to PPP-10 were mounted on a GTO52 Dahlgren sheetfed press and the amount of pages needed before the background and image areas were toning-free (on press clean-out), were determined. Each print job was started using K+E Novavit 800 Skinnex ink (trademark of BASF Druckfarben GmbH) and 4 wt % Prima FS404 (trademark of Agfa Graphics) in water as fountain solution. A compressible blanket was used and printing was performed on non-coated offset paper. The press was start-up in such a way that both ink and fountain were already from the first press revolution (and paper contact) available on the printing plates.

5. Results

The amount of pages needed for clean-out of the printing plates was assessed at page 0, 50, 100 and 150. This clean-out is characterized by the complete removal of the coating in non-imaged areas resulting in toning-free prints of these non-imaged parts.

In addition, image areas which are not composed of a full solid should print according to their imaged density and thus not exhibit plugging, i.e. dotgain of the high density screens.

The clean-out results of PP-08 to PP-10 are summarized in Table 9.

TABLE 9

Clean-out behaviour of printing plates PP-08 to PP-10

| Printing plate precursor | Amount of inventive compound in the dry layer | Clean-out* achieved at page |
| --- | --- | --- |
| PP-08 | — | 100 |
| PP-09 | 9% wt | 50 |
| PP-10 | 99% wt | 1 |

*Clean out is determined as defined above

The clean out results in Table 9 demonstrate that the inventive compound in the overcoat layer significantly improves the clean-out behaviour of the printing plate.

The invention claimed is:

1. A lithographic printing plate precursor including, on a support, a photopolymerisable layer and an overcoat layer provided on top of the photopolymerisable layer,
wherein the overcoat layer includes a compound comprising at least one moiety having a structure according to Formula (I):

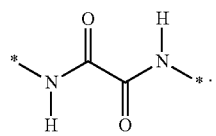 [SMILES: *NC(=O)C(=O)N*]

wherein each * independently denotes a linking position to the rest of the compound.

2. The printing plate precursor according to claim 1, wherein the compound is represented by Formula (II):

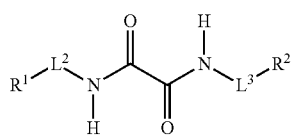

wherein
$R^1$ and $R^2$ independently represent a terminal group; and
$L^2$ and $L^3$ independently represent a divalent linking group.

3. The printing plate precursor according to claim 2, wherein the terminal groups $R^1$ and $R^2$ are represented by hydrogen, an optionally substituted alkyl or cycloalkyl group, an optionally substituted aryl group, an optionally substituted aralkyl group or an optionally substituted heteroaryl group.

4. The printing plate precursor according to claim 2, wherein the divalent linking groups $L^2$ and $L^3$ independently represent an optionally substituted alkylene or cycloalkylene group.

5. A method for making a lithographic printing plate precursor comprising:
applying on a support a photopolymerisable layer and an overcoat layer as defined in claim 1; and
drying the precursor.

6. A method for making a printing plate comprising:
image-wise exposing the printing plate precursor as defined in claim 1 to heat and/or light; and
developing the precursor.

7. The method according to claim 6, wherein the precursor is exposed with laser light having a wavelength between 350 and 450 nm.

8. The method according to claim 6, wherein the precursor is exposed with laser light having a wavelength between 750 and 1500 nm.

9. The method according to claim 6, wherein the developing step is carried out on press by mounting the exposed precursor on a plate cylinder of a lithographic printing press and rotating the plate cylinder while feeding dampening liquid and/or ink.

10. The method according to claim 6, wherein the developing step is carried out off-press by treating the exposed precursor with a gum solution and whereby the precursor is developed and gummed in one single step.

11. The printing plate precursor according to claim 3, wherein the divalent linking groups $L^2$ and $L^3$ independently represent an optionally substituted alkylene or cycloalkylene group.

12. A method for making a lithographic printing plate precursor comprising:
applying on a support a photopolymerisable layer and an overcoat layer as defined in claim 2; and
drying the precursor.

13. A method for making a printing plate comprising:
image-wise exposing the printing plate precursor as defined in claim 2 to heat and/or light; and
developing the precursor.

14. A method for making a lithographic printing plate precursor comprising:
applying on a support a photopolymerisable layer and an overcoat layer as defined in claim 3; and
drying the precursor.

15. A method for making a printing plate comprising:
image-wise exposing the printing plate precursor as defined in claim 3 to heat and/or light; and
developing the precursor.

16. A method for making a lithographic printing plate precursor comprising:
applying on a support a photopolymerisable layer and an overcoat layer as defined in claim 4; and
drying the precursor.

17. A method for making a printing plate comprising:
image-wise exposing the printing plate precursor as defined in claim 4 to heat and/or light; and
developing the precursor.

18. The method according to claim 7, wherein the developing step is carried out on press by mounting the exposed precursor on a plate cylinder of a lithographic printing press and rotating the plate cylinder while feeding dampening liquid and/or ink.

19. The method according to claim 7, wherein the developing step is carried out off-press by treating the exposed precursor with a gum solution and whereby the precursor is developed and gummed in one single step.

20. The method according to claim 8, wherein the developing step is carried out on press by mounting the exposed precursor on a plate cylinder of a lithographic printing press and rotating the plate cylinder while feeding dampening liquid and/or ink.

\* \* \* \* \*